United States Patent [19]
Lee et al.

[11] Patent Number: 5,700,762
[45] Date of Patent: Dec. 23, 1997

[54] SUBSTITUTED BENZOYL (HETERO) CYCLIC DIONES

[75] Inventors: Shy-Fuh Lee, Sunnyvale, Calif.; Takashi Nishizaka; Kenichi Komatsubara, both of Kawasaki, Japan

[73] Assignee: Sandoz Ltd., Basel, Switzerland

[21] Appl. No.: 448,008

[22] Filed: May 23, 1995

Related U.S. Application Data

[63] Continuation of Ser. No. 411,086, Sep. 22, 1989, Pat. No. 5,623,124, which is a continuation-in-part of Ser. No. 182,534, Apr. 18, 1988, abandoned.

[51] Int. Cl.$^6$ .................................................. A01N 43/16
[52] U.S. Cl. ................................................. 504/292; 549/397
[58] Field of Search ............................. 549/417, 397; 504/292

[56] References Cited

U.S. PATENT DOCUMENTS 4,728,745  3/1988  Carter et al. ........................... 549/417

FOREIGN PATENT DOCUMENTS 0186117  7/1986  European Pat. Off. ............... 549/417

*Primary Examiner*—James H. Reamer
*Attorney, Agent, or Firm*—Lynn Marcus-Wyner

[57] ABSTRACT

Substituted aryl or heteroaryl in particular benzoyl bicycloalkanediones and related compounds, intermediates therefor, synthesis thereof, and the use of said diones for the control of weeds.

23 Claims, No Drawings

SUBSTITUTED BENZOYL (HETERO) CYCLIC DIONES

This is a Continuation of application Ser. No. 07/411,086, filed on Sep. 22, 1989, now U.S. Pat. No. 5,623,124 which is a Continuation-In-Part of applicaiton Ser. No. 07/182,534, filed on Apr. 18, 1988, now abandoned.

This invention relates to novel substituted aryl or heteroaroyl, in particular benzoyl, bicycloalkanediones and related compounds, intermediates therefor, synthesis thereof, and the use of said compounds for the control of weeds and acari.

More particularly, this invention concerns compounds of the general formula

wherein A is a bicyclic 1-one-2-ene-3-ol-2yl residue;

B is an aryl or heteroaryl group optionally bearing substituents; and salts, enolethers and enolesters thereof.

A particular group of compounds is that represented by formula I

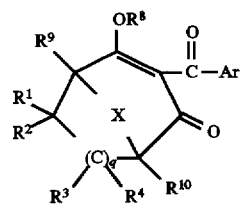

wherein,

Ar is selected from the groups

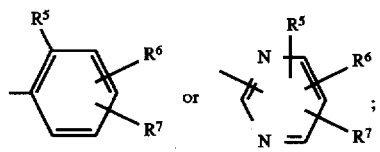

X is oxygen, sulfur or $C_{1-4}$alkylene;

each of $R^1$, $R^2$, $R^3$, $R^4$, $R^9$ and $R^{10}$ is, independently, hydrogen, $C_{1-8}$alkyl or $COOR^{16}$;

$R^5$ is $C_{1-8}$alkyl, optionally substituted with one to six halogen atoms; $C_{1-8}$alkoxy, optionally substituted with one to six halogen atoms; ($C_{1-8}$alkyl) carbonyl; ($C_{1-8}$alkoxy) carbonyl; $NR^{13}R^{14}$; $O_nS(O)_{n'}R^{12}$; $NR^{15}SO_2R^{12}$; halogen; cyano; or nitro;

each of $R^6$ and $R^7$ is independently hydrogen or selected from the values of $R^5$; or $R^6$ and $R^7$ together form the group -Y-W-Z-;

$R^8$ is hydrogen, $C_{1-8}$alkyl, optionally substituted ($C_{1-8}$alkyl)carbonyl, optionally substituted ($C_{1-8}$alkoxy) carbonyl, $C(O)NR^{13}R^{14}$, $C_{1-8}$alkylsulfonyl, $P(O)$—$(OR^{11})_2$, $R^{13}P(O)OR^{11}$ or optionally substituted benzoyl or a salt forming moiety;

$R^{11}$ is $C_{1-8}$alkyl;

$R^{12}$ is $C_{1-8}$alkyl, optionally substituted with one to six halogen atoms;

each of $R^{13}$, $R^{14}$, $R^{15}$ and $R^{16}$ is, independently, hydrogen or $C_{1-8}$alkyl;

each of $R^{17}$ and $R^{18}$ is independently hydrogen, halogen, or $C_{1-8}$alkyl optionally substituted with one to six halogen atoms; or $R^{17}$ and $R^{18}$ together form an oxo group;

each of $R^{19}$ and $R^{20}$ is, independently, hydrogen, halogen, or $C_{1-8}$alkyl optionally substituted with one to six halogen atoms;

W is $-(CR^{17}R^{18})_t-(CR^{19}R^{20})_{t'}-$ or $SO_2$;

each of Y and Z is independently oxygen, sulfur, $SO_2$, C=O or $CR^{15}R^{16}$; with the proviso that Y and Z are attached to adjacent carbons;

n is zero or one;

n' is zero, one or two;

q is zero, one or two;

t is one or two; and t' is zero or one.

Enol compounds of the formula (I), wherein $R^8$ is H, can exist in a number of tautomeric forms, the following being representative;

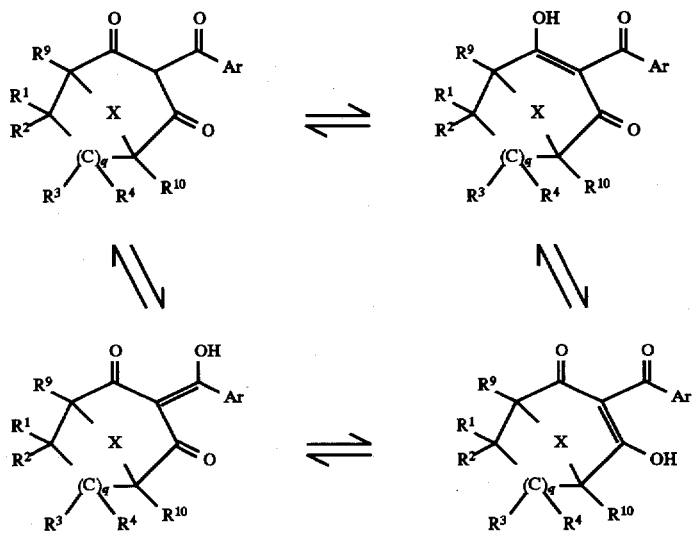

It is intended that all such tautomeric structures are included within the scope of this invention.

In the description and claims hereinafter, each of W, X, Y, Z, n, n', q, t, t' and $R^1$–$R^{20}$ is as defined above, unless otherwise specified.

In the practice of the present invention, X is preferably oxygen or $C_{1-2}$alkylene, especially $C_{1-2}$alkylene, particularly —$CH_2$—.

Ar is preferably substituted phenyl.

Where any of the substituents $R^5$–$R^7$, $R^{12}$ and $R^{17}$–$R^{20}$ is or comprises halogen, such halogen is conveniently selected from bromo, chloro and fluoro.

Where any of $R^1$–$R^{20}$ is or comprises $C_{1-8}$alkyl, it is preferably of one to four carbons.

Where any of $R^5$–$R^8$ is or comprises $C_{1-8}$alkoxy, it is preferably of one to four carbons.

Each of $R^1$–$R^4$, $R^9$ and $R^{10}$ is preferably hydrogen or $C_{1-4}$alkyl; such alkyl is more preferably of one to three carbons; each of $R^1$–$R^4$, $R^9$ and $R^{10}$ is more preferably hydrogen.

$R^5$ conveniently signifies hydrogen, $C_{1-4}$alkyl optionally substituted with halogen, —(O)$_n$—S(O)$_n$,—$C_{1-4}$alkyl, halogen or nitro. It is preferably methyl, $CF_3$, $C_{1-3}$alkylsulfonyl, $C_{1-3}$alkylsulfonyloxy, chloro, bromo or nitro especially nitro.

$R^6$ is preferably hydrogen, $C_{1-4}$alkyl, $C_{1-4}$alkoxy, bromo, chloro or, together with $R^7$, the group -Y-W-Z-; it is more preferably hydrogen, methoxy or chloro, or, together with $R^7$, methylenedioxy; more preferably hydrogen.

$R^7$ is preferably bromo, chloro, fluoro, $OSO_2C_{1-4}$alkyl, $SO_2C_{1-4}$alkyl, $OSO_2C_{1-4}$haloalkyl, $SC_{1-4}$alkyl, $SOC_{1-4}$alkyl, $NR^{15}SO_2C_{1-4}$alkyl, or, together with $R^6$, the group -Y-W-Z-. It is more preferably chloro, fluoro, bromo, $C_{1-3}$alkylthio, $C_{1-3}$alkylsulfonyl or $C_{1-3}$alkylsulfonyloxy, or, together with R6, methylenedioxy.

Examples of various preferred compound groups comprising $R^8$ are (a) $R^8$-hydrogen, $C_{1-8}$alkyl, ($C_{1-8}$alkyl) carbonyl, ($C_{1-8}$alkoxy)carbonyl, $C(O)NR^{13}R^{14}$, $C_{1-8}$alkylsulfonyl P(O)—(OR$^{11}$)$_2$, $R^{13}$P(O)OR$^{11}$ or benzoyl or a salt forming moiety (b) $R^8$-hydrogen, $C_{1-4}$alkyl, $C_{1-4}$alkylcarbonyl, benzoyl or $C_{1-4}$alkylsulfonyl (c) hydrogen, methyl, ethyl, t-butylcarbonyl, isobutylcarbonyl, benzoyl or methylsulfonyl (d) hydrogen (e) optionally substituted ($C_{1-8}$alkyl)carbonyl, optionally substituted ($C_{1-8}$alkoxy)carbonyl, optionally substituted benzoyl (f) ($C_{1-8}$alkoxy)carbonyl.

Where $R^8$ is a salt forming moiety, it may be inorganic e.g. a metal equivalent of Na, Ca, Fe or Cu; or organic, e.g., the ammonium salt moiety of an amine e.g. 1-(methylaminomethyl)naphthalene), a sulfonium, sulfoxomium or phosphonium moiety. Preferred examples of ammonium salts are those derived from amines having the Formula X.

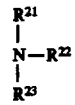  (X)

wherein each of $R^{21}$, $R^{22}$ and $R^{23}$ represents independently hydrogen, $C_{1-16}$alkyl optionally substituted by one or more hydroxy groups, $C_{2-4}$alkenyl or $R^{21}$ and $R^{22}$ form together a $C_{2-5}$alkylene group which may optionally be interrupted by oxygen. Depending on the nature of $R^8$, the salt may exist in chelated form.

Where $R^8$ is substituted ($C_{1-8}$alkyl)— or ($C_{1-8}$alkoxy) carbonyl it is preferably substituted by 1 to 4 halogen atoms selected from fluorine, chlorine and bromine.

q is preferably 1 or 2.

$R^{12}$ is preferably methyl or ethyl.

Preferably $R^6$ is in the 3-position and $R^7$ is in the 4-position.

Combinations of this preferred substituents are especially preferred.

Preferred particular compounds are those numbered 8, 10, 27, 30, 36 and 37.

The compounds of the present invention of formula I are new substances which can be prepared by methods analogous to methods known in the art for the preparation of 2-aroyl-(bicyclic-1,3-diones) and enol ethers or enol esters thereof.

More particularly, they can be obtained by, for example: reacting an enol ester of formula (II)

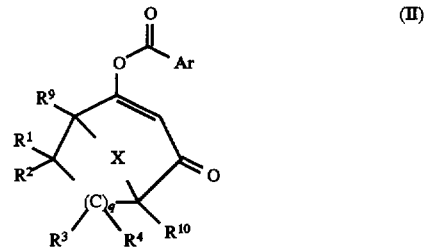

wherein Ar, X, q, $R^1$–$R^4$ and $R^9$–$R^{10}$ are as defined above, with a cyanide source and a moderate base to give a compound of formula I where $R^8$ is hydrogen, followed, where desired, by etherification or esterification to the corresponding enol ethers or enol esters.

The above reaction is carried out in the presence of a catalytic amount of a source of cyanide anion and/or hydrogen cyanide, together with a molar excess, with respect to the enol ester, of a moderate base. The reaction is conveniently carried out in a solvent which is inert under the reaction conditions, e.g. 1,2-dichloroethane, toluene, acetonitrile, methylene chloride, ethyl acetate, dimethylformamide (DMF) and methyl isobutyl ketone (MIBK). In general, depending on the nature of the reactants and the cyanide source, the rearrangement may be conducted at temperatures up to about 80° C. In some cases, for instance when there is a possible problem of excessive by-product formation, the temperatures should be kept at about 40° C. maximum.

Preferred cyanide sources are alkali metal cyanides such as sodium and potassium cyanide; cyanohydrins of methyl alkyl ketones having from 1–4 carbon atoms in the alkyl groups, such as acetone or methyl isobutyl ketone cyanohydrins; cyanohydrins of benzaldehyde or of $C_2$–$C_5$ aliphatic aldehydes such as acetaldehyde, propionaldehyde, etc., cyanohydrins; zinc cyanide; tri(lower alkyl)silyl cyanides, notably trimethylsilylcyanide; and hydrogen cyanide itself. Among cyanohydrins the preferred cyanide source is acetone cyanohydrin. The cyanide source is used in an amount up to about 50 mole percent based on the enol ester. Generally about 1–10 mole % of the cyanide source is preferred.

By the term "moderate base" is meant a substance which acts as a base yet whose strength or activity as a base lies between that of strong bases such as hydroxides (which could cause hydrolysis of the enol ester) and that of weak bases such as bicarbonates (which would not function effectively). Moderate bases suitable for use in this reaction include both organic bases such as tertiary amines and inorganic bases such as alkali metal carbonates and phosphates. Suitable tertiary amines include trialkylamines such as triethylamine, trialkanolamines such as triethanolamine, and pyridine. Suitable inorganic bases include potassium carbonate and trisodium phosphate. The base is used in an amount of from about 1 to about 4 moles per mole of enol ester, preferably about 1.3–2 moles per mole.

When the cyanide source is an alkali metal cyanide, particularly potassium cyanide, a phase transfer catalyst may be included in the reaction. Particularly suitable phase transfer catalysts are the Crown ethers.

Depending on the reaction conditions, the thus obtained keto-enol compounds may be in free acid form ($R^8$ is H) or in salt form; where they are in salt form (i.e. $R^8$ is a salt forming moiety), $R^8$ may be inorganic (e.g. a metal equivalent of Na, Ca, Fe or Cu) or organic, e.g. the ammonium salt moiety of an amine, sulfonium, sulfoxmium or phosphonium moiety. Depending on the nature of $R^8$, the salt may exist in chelated form. The salt form may be converted to the corresponding acid form ($R^8$ is H) in a manner known per se, and vice versa.

Compounds of formula I where $R^8$ is other than hydrogen or a salt forming moiety can be prepared in a manner known per se for the preparation of enol ethers or enol esters from the corresponding enol compounds, e.g. by reacting a compound of formula I where $R^8$-H with either a) the group $R^8$-OH and a catalyst, or b) the group $R^8$-Q and a moderate base, wherein Q is a halogen atom, to give a compound of formula I where $R^8$ is as defined above other than hydrogen or a salt forming moiety.

The above reaction a) is carried out in the presence of a catalyst such as concentrated sulfuric acid. The reaction is conveniently carried out in a solvent which is also the reactant such as methanol, and at an elevated temperature.

The above reaction b) is carried out in the presence of a moderate base such as triethylamine or pyridine and conveniently at RT or below.

The compounds of formula I may be recovered from the reaction mixture in which they are formed by working up by established procedures.

The starting materials and reagents employed in the process described herein are either known or, insofar as they are not known, maybe produced in a manner analogous to the processes described herein or to known processes.

The novel compounds of formula I are useful for the control of weeds, using pre- and/or post-emergent treatments. Compounds of formula I are also useful as plant growth regulators and as acaricides. The compounds can be applied for example in the form of dusts, granules, solutions, emulsions, wettable powders, flowables and suspensions. Application of a compound of the present invention as a herbicide is made according to conventional procedure to the weeds or their locus using one-half or less to ten pounds or especially one-tenth or less (e.g. one-fiftieth) to ten pounds per acre (ca 0.56 to 11.2 especially 0.112 to 11.2 kg/ha). Application as a selective herbicide in rice is made for example at a rate of ca 5 to 1000 g preferably 10 to 500 g especially 20 to 200 g per hectare. The application of a compound of the present invention to the "locus" of the weed included application to the seeds, the plant (weed) or parts of the plant or the soil.

The term "herbicide," as used herein, refers to an active ingredient which modifies the growth of plants because of phytotoxic or plant growth regulating properties so as to retard the growth of the plant or damage the plant sufficiently to kill it.

The compounds of the present invention, when applied as either post or pre-emergents, demonstrate high levels of herbicidal activity on broadleaf, grass and sedge weeds.

Thus the compounds are useful in combatting weeds in corn (e.g. especially compound 30 hereinafter) and wheat without damaging crop cultures. Both grassy and broadleaf weeds are controlled with control of the latter being particularly good.

Compounds of the invention exhibit selectivity in various crops. Additionally certain compounds of formula I such as those wherein $R^8$ is hydrogen or especially has the meanings given above under e) and f) or is an ammonium salt derived from an amine of formula X as defined above exhibit acceptable rice tolerance with excellent weed control and are thus useful for combatting weeds in rice especially in transplanted (paddy) rice.

Compounds of this type wherein X is $CH_2$ and each of $R^1$, $R^2$, $R^3$, $R^4$, $R^9$ and $R^{10}$ is hydrogen and Ar is o-nitro-p-$(O_nS(O)_n$, $R^{12})$-phenyl are especially preferred for this use (e.g. especially compounds 8, 36 and 37 hereinafter). Examples of weeds which may be selectively combatted by both pre- and post-emergent application in rice include Echinochloa spp e.g. barnyard grass, Cyperus spp e.g. flatsedge, bullrush, spikerush, water nutsedge, Rumex spp, Sagitaria spp e.g. arrowhead, Monochoria spp and Serbania spp. They have an excellent herbicidal activity on weeds prior to germination and during growth and are useful as herbicides for soil treatments before and after transplantation of young rice plants, during the growth of crops and for culm and foliage treatments before transplantation and during the growth of crops. The invention also provides herbicidal commmpositions suitable for use in rice locus.

In the use of the compounds of formula I as a herbicide or acaricide, a compound of formula I, or mixtures thereof, can conveniently be employed as agricultural compositions in association with acceptable diluent(s) for application to the weed, aracri, or their loci. Such compositions also form part of the present invention.

Methods of preparing suitable compositions which can be used with a compound of the present invention are described in the literature along with suitable liquid and solid carriers, such as in U.S. Pat. Nos. 4,192,669 and 4,163,661, which are incorporated herein by reference. The optimum usage of a compound of the present invention will depend on various factors such as weed to be treated, incidence and/or growth of weeds, weather, environmental conditions, formulation, application method, locus, timing and the like and is readily determinable by one of ordinary skill in the art using routine testing such as greenhouse testing and small plot testing.

The compounds of the present invention can be compounded with appropriate inert carriers, if necessary, and additivies in an appropriate ratio by means of dissolving, separating, suspending, mixing, impregnating, adsorbing or precipitating operation to formulate into dusts, suspensions, suspension concentrates, emulsions, solutions, wettable powders, flowables, granules or tablets.

A wide variety of solids and liquids can be used as the inert diluents or carriers in the present invention. Examples of materials which can be used as the solid carriers include vegetable powders such as soybean meal, corn meal, wood meal, bark meal, sawdust, tobacco stem meal, walnut shell flour, bamboo meal, fibrous meal and residue after the extraction of vegetable extract; synthetic polymers such as crushed synthetic resins; inorganic mineral powders such as clay (e.g., kaolin, bentonite, terra abla), talc (e.g. talc, pyrophylite), silica (e.g. diatomaceous earth, siliceous sand, mica, white carbon [synthetic colloidal silica called hydrated fine silicon powder, hydrated silicic acid, or a product mainly composed of calcium silicate], activated carbon, sulfur powder, pumice stone, calcined diatomaceous earth, crushed brick, fly ash, sand, calcium carbonate and calcium phosphate; and chemical fertilizers such as ammonium sulfate, ammonium phosphate and ammonium nitrate and compost. These diluents or carriers may be used either alone or in a combination of two or more of them. As the liquid carriers, there can be used materials which themselves have an ability as solvent as well as materials which themselves do not have an ability as solvent, but can disperse active ingredients by the aid of other additives. Examples of the materials which can be used as the liquid carriers include water, alcohols (e.g., methanol, ethanol, isopropanol, butanol, ethylene glycol), ketones (e.g., acetone, methyl ethyl ketone, methyl sobutyl ketone, diisobutyl ketone, cyclohexanone), ethers (e.g., ethyl ether, dioxane, cellosolve, dipropyl ether, tetrahydrofuran), aliphatic hydrocarbons (e.g., gasoline, diesel oil, mineral oil), aromatic hydrocarbons (e.g., benzene, toluene, xylene, solvent naphtha, alkylnaphthalenes), halogenated hydrocarbons (e.g., dichloroethane, chlorinated benzene, chloroform, carbon tetrachloride), esters (e.g., ethyl acetate, dibutyl phthalate, diisopropyl phthalate, dioctyl phthalate), acid amides (e.g., dimethylformamide, diethylformamide, dimethylaceamide), nitriles (e.g., acetonitrile) and dimethyl sulfoxide. These liquid carriers maybe used either alone or as a mixture of two or more of them.

In some cases, other additives are used either alone or as a mixture of two or more. In some cases, no additive is used. Surfactants are used for the purposes of emulsifying, dispersing, spreading, solubilizing and/or wetting the compounds as active ingredients. Examples of the surfactants include polyoxyethylene alkylaryl ethers, polyoxyethylene alkyl ethers, polyoxyethylene higher fatty acid esters, lauryl sulfate, polyoxyethylene resin acid esters, polyoxyethylene sorbitan monolaurate, polyoxyethylene sorbitan moooleate, alkylarylsulfonates, naphthalenesulfonic acid condensate, lignosulfonates and higher alcohol sulfuric esters. For the purposes of dispersion-stabilizing, tackifying and bonding the compound of the active ingredients, there can be used, for example, casein, gelatin, starch, alginic acid, methyl cellulose, carboxymethyl cellulose, gum arabic, polyvinyl alcohol, pine oil, tung oil, bentonite and lignosulfonates.

For the purpose of improving the fluidity of solid products, there may be used wax, stearates and alkyl phosphates.

Naphthalenesulfonate condensates and condensed phosphates may be used as peptizers for suspension products.

If desired, anti-foaming agents such as silicone oil, anti-caking agents or anti-corrosion agents may be added.

Alternatively, the compounds of formula I may be used in micro-encapsulated form.

The compounds of formula I can be combined with a cyclodextrin to make a cyclodextrin inclusion complex for application to the pest or weed or its locus.

Suitable formulations contain from 0.01 to 99% by weight of active ingredient, from 0 to 20% of surfactant and from 1 to 99.99% of solid or liquid diluent(s). Higher ratios of surfactant to active ingredient are sometimes desirable and are achieved by incorporation into the formulation or by tank mixing. Application forms of a composition generally contain between 0.01 and 25% by weight of active ingredient. For example powders or granules may in general contains 0.2 to 20% by weight of active ingredient. Emulsions or wettable formulations will generally contain 0.1 to 50% by weight of active ingredients. Lower or higher levels of active ingredient can, of course, be present depending on the intended use, the physical properties of the compound and the mode of application. Concentrate forms of a composition intended to be diluted before use generally contain between 2 and 90%, preferably between 5 and 81% by weight of active ingredient.

EXAMPLE A

Preparation of a Dust

10 Parts of a compound according to this invention and 90 parts of powdered talc are mixed in a mechanical grinder-blender and are gound until a homogeneous, free-flowing dust of the desired particle size is obtained. This dust is suitable for direct application to the site of the weed, acari infestation.

EXAMPLE B

Preparation of a Wettable Powder

25 Parts of a compound according to this invention are mixed and milled with 25 parts of synthetic fine silica, 2 parts of sodium lauryl sulphate, 3 parts of sodium ligninsulphonate and 45 parts of finely divided kaolin until the mean particle size is about 5 micron. The resulting wettable powder is diluted with water before use to a spray liquor with the desired concentration.

EXAMPLE C

Preparation of Emulsifiable Concentrate (EC)

13.37 Parts of a compound according to this invention are mixed in a beaker with 7.04 parts of Toximul 360A (a mixture of anionic and non-ionic surfactants containing largely anionic surfactants), 23.79 parts of dimethylformamide and 55.8 parts of Tenneco 500–100 (predominantly a mixture of alkylated aromatics such as xylene and ethylbenzene) until solution is effected. The resulting EC is diluted with water for use.

EXAMPLE D

Wettable Powder 50 parts of the compound No. 36, 20 parts of diatomaceous earth, 22 parts of clay, 3 parts of white carbon, 2 parts of sodium lignosulfonate and 3 parts of sodium alkylnaphthalenesulfonate were mixed and crushed to obtain a wettable powder containing 50% of the active ingredient.

EXAMPLE E

Granule 0.35 parts oft he compound No. 37, 25 parts of bentonite, 70.65 parts of talc, 2 parts of sodium dodecylbenzenesulfonate and 2 parts of sodium lignosulfonate were mixed. About 20 parts of water was added thereto. The mixture was headed in a kneader, granulated in a granulator and dried. Dressing of grain was conducted to obtain a granule containing 0.35% of the active ingredient.

The compositions of this invention can also comprise other compounds having biological activity, e.g. compounds having similar or complementary herbicidal activity for broadspectrum weed control or compounds having acaricidal activity or compounds having antidotal, fungicidal, insecticidal or insect attractant activity.

The following examples are provided to illustrate the practice of the present invention. Temperature is given in degrees Centigrade. RT means room temperature. Parts and percentages are by weight.

PREPARATION OF FINAL COMPOUNDS

EXAMPLE 1

To a solution of 4-(4-chloro-2-nitrobenzoyloxy)-bicyclo-[3,2,1]-3-octen-2-one (0.75 g) in 12 ml of acetonitrile are added triethylamine (0.62 ml) and acetone cyanohydrin (0.15 ml) in one portion. The mixture is stirred at RT overnight, after which the acetonitrile is removed and the residue is taken up in methylene chloride, then washed with dil. HCl and with brine, dried and evaporated to dryness. The crude product is purified by PTLC to give 3-(4-chloro-2-nitrobenzoyl)-bicyclo-[3,2,1]octane-2,4-dione (compound 1, Table A).

EXAMPLE 2

To a solution of 4-(4-chloro-2-nitrobenzoyloxy)-5,8,8-trimethyl-bicyclo[3,2,1]-3-octen-2-one (4.20 g) in 25 ml of acetonitrile are added triethylamine (3.2 ml, 2 eq.) and acetone cyanohydrin (0.4 ml), and the mixture is stirred at RT for 16 hr. The acetonitrile is removed, and the residue is concentrated and purified by PTLC to give 3-(4-chloro-2-nitrobenzoyl)-1,8,8-trimethylbicyclo[3,2,1]octane-2,4-dione (compound 12, Table A).

EXAMPLE 3

To a solution of 4-(3-methoxy-4-methylsulfonyloxy-2-nitrobenzoyloxy)-bicyclo[3,2,1]-3-octen-2-one (17.6 mmol) in 50 ml of acetonitrile are added triethylamine (4.91 ml, 2 eq.) and acetone cyanohydrin (1.0 ml) in one portion. The mixture is stirred at RT overnight, after which it is diluted with water and extracted with ether. The ether is removed and the residue is purified by PTLC to give 3-(3-methoxy-4-methylsulfonyloxy-2-nitrobenzoyl)-bicyclo[3,2,1]octane-2,4-dione (compound 9, Table A).

EXAMPLE 4

To a solution of 4-(4-methylsulfonyloxy-2-chlorobenzoyloxy)bicyclo-[3,2,1]-3-octen-2-one (14.3 mmol) in 25 ml of acetonitrile are added triethylamine (3.97 ml, 2 eq.) and acetone cyanohydrin (0.4 ml), and the mixture is stirred at RT overnight. The acetonitrile is removed, and the residue is taken up in water and extracted with methylene chloride. The combined organic extracts are washed with dilute HCl and with brine, dried and evaporated to dryness. The crude product is purified from ether to give 3-(4-methylsulfonyloxy-2-chlorobenzoyl)bicyclo[3,2,1]octane-2,4-dione (compound 4, Table A).

EXAMPLE 5

To a solution of 4-(3,4-methylenedioxy-2-nitrobenzoyloxy)bicyclo-[3,2,1]-3-octen-2-one (13.2 mmol) in 50 ml of acetonitrile are added triethylamine (3.69 ml) and acetone cyanohydrin (0.5 ml) in one portion. The mixture is stirred at RT for 2 days, after which it is diluted with water and extracted with ether. The ether is removed and the residue is purified by PTLC to give 3-(3,4-methylenedioxy-2-nitrobenzoyl)bicyclo-[3,2,1]octane-2,4-dione (compound 11, Table A).

EXAMPLE 6

To a solution of 4-(4,5-methylenedioxy-2-nitrobenzoyloxy)bicyclo-[3,2,1]-3-octen-2-one (14.4 mmol) in acetonitrile are added triethylamine (4.0 ml, 28.8 mmol) and acetone cyanohydrin (0.4 ml), and the mixture is stirred at RT overnight. The acetonitrile is removed, and the residue is taken up in water and extracted with methylene chloride. The combined organic extracts are washed with dilute HCl and with brine, dried and evaporated to dryness. The crude product is purified by chromatography to give 3-(4,5-methylenedioxy-2-nitrobenzoyl)-bicyclo [3,2,1]octane-2,4-dione.

EXAMPLE 7

Following the procedure of any of Examples 1 through 6, each of the compounds under Table A is prepared by rearrangement of the corresponding enol ester.

EXAMPLE 8

A solution of 3-(4-chloro-2-nitrobenzoyl)-bicyclo[3,2,1]-octane-2,4-dione (2.54 mmol) and 2 drops of conc. sulfuric acid in 20 ml of methanol is heated under reflux for 48 hours. The reaction mixture is concentrated and the residue is taken up in ether. The ethereal solution is washed with aqueous sodium bicarbonate and with brine, dried and evaporated to dryness to give 2-methoxy-3-(4-chloro -2-nitrobenzoyl) bicyclo-[3,2,1]-octane-4-one.

EXAMPLE 9

To a mixture of 3-(4-chloro-2-nitrobenzoyl)-bicyclo -[3, 2,1]-octane-2,4-dione (2.26 mmol) in methylene chloride (10 ml) containing triethylamine (0.47 ml, 3.39 mmol) is added dropwise at 0° a solution of acetyl chloride (0.27 g, 3.39 mmol) in 5 ml of methylene chloride. The resulting mixture is stirred for 30 min., and is then diluted with methylene chloride, washed, dried and evaporated to dryness to give 4-acetoxy-3-(4-chloro-2-nitrobenzoyl)-bicyclo [3,2,1]-3-octen-2-one.

EXAMPLE 10

Following the procedure of Example 9, the final compounds under column I are prepared by the reaction of 3-(4-chloro-2-nitrobenzoyl)-bicyclo[3,2,1]octane-2,4-dione with the corresponding acyl chloride.

I 31. 4-propionyloxy-3-(4-chloro-2-nitrobenzoyl)-bicyclo-[3, 2,1]-3-octen-2-one
32. 2-isobutyryloxy-3-(4-chloro-2-nitrobenzoyl)-bicyclo-[3, 2,1]-3-octen-2-one
33. 2-pivaloyloxy-3-(4-chloro-2-nitrobenzoyl)-bicyclo-[3,2, 1]-3-octen-2-one
34. 2-benzoyloxy-3-(4-chloro-2-nitrobenzoyl)-bicyclo-[3,2, 1]-3-octen-2-one
35. 4-pivaloyloxy-3-(4-chloro-2-nitrobenzoyl)-bicyclo-[3,2, 1]-3-octen-2-one (foam)

EXAMPLE 11

Preparation of 4-benzoyloxy-3-(4-methylsulfonyl-2-nitrobenzoyl)-bicyclo-[3,2,1]-3-octen-2-one (compound no. 36)

To a solution of 2.0 g of 3-(4-methylsulfonyl-2-nitrobenzoyl)-bicyclo-[3,2,1]-octane-2,4-dione and 0.8 g of triethylamine in 30 ml of methylene dichloride is added 0.77 g of benzoyl chloride in 5 ml of methylene dichloride at 0° and the mixture stirred for one hour at 0°. The resulting solution is diluted with methylene dichloride, washed with brine, dried and evaporated to dryness. The crude product is purified by silica gel column chromatography to give the solid which is washed with isopropyether m.p. 142°–144°.

EXAMPLE 12

Preparation of the triethylammonium salt of 4-hydroxy-3-(4-methylsulfonyl-2-nitrobenzoyl)-bicyclo-[3,2,1]-3-octen-2-one (compound no. 37)

0.8 g of 3-(4-methylsulfonyl-2-nitrobenzoyl) -bicyclo-[3, 2,1]-octane-2,4-dione and 0.5 ml of triethylamine are stirred in 20 ml of methylene dichloride at RT for one hour. Evaporation of the solution and recrystalization from isopropylether gave the title compound m.p. 126°–7°.

TABLE A

| Cpd | X | q | R⁹ | R¹⁰ | R⁵ | R⁶ | R⁷ | m.p. (°C.) |
|---|---|---|---|---|---|---|---|---|
| 1 | CH₂ | 1 | H | H | NO₂ | H | Cl | 134 |
| 2 | CH₂ | 1 | H | H | NO₂ | H | Br | 142 |
| 3 | CH₂ | 1 | H | H | Cl | H | SO₂CH₃ | foam |
| 4 | CH₂ | 1 | H | H | Cl | H | OSO₂CH₃ | |
| 5 | CH₂ | 1 | H | H | Cl | Cl | Cl | |
| 6 | CH₂ | 1 | H | H | Cl | Cl | SO₂CH₃ | |
| 7 | CH₂ | 1 | H | H | CH₃ | H | Br | 92–95 |
| 8 | CH₂ | 1 | H | H | NO₂ | H | SO₂CH₃ | 148 |
| 9 | CH₂ | 1 | H | H | NO₂ | OCH₃ | OSO₂CH₃ | |
| 10 | CH₂ | 1 | H | H | NO₂ | H | OSO₂CH₃ | 140 |
| 11 | CH₂ | 1 | H | H | NO₂ | —O—CH₂—O— | | |
| 12 | C(CH₃)₂ | 1 | H | CH₃ | NO₂ | H | Cl | 101 |
| 13 | O | 1 | CH₃ | CH₃ | NO₂ | H | Cl | foam |
| 14 | O | 1 | CH₃ | CH₃ | NO₂ | H | Br | |
| 15 | O | 1 | CH₃ | CH₃ | CH₃ | H | Br | |
| 16 | O | 1 | CH₃ | CH₃ | Cl | Cl | Cl | |
| 17 | O | 1 | CH₃ | CH₃ | Cl | Cl | SO₂CH₃ | |
| 18 | O | 1 | CH₃ | CH₃ | Cl | H | SO₂CH₃ | |
| 19 | O | 1 | CH₃ | CH₃ | NO₂ | H | SO₂CH₃ | |
| 20 | O | 1 | CH₃ | CH₃ | NO₂ | OCH₃ | OSO₂CH₃ | |
| 21 | O | 1 | CH₃ | CH₃ | Cl | H | OSO₂CH₃ | |
| 22 | O | 1 | CH₃ | CH₃ | NO₂ | H | OSO₂CH₃ | |
| 23 | CH₂ | 1 | H | H | NO₂ | H | SCH₂CH₃ | 75 |
| 24 | CH₂ | 1 | H | H | CH₃ | H | Cl | 94 |
| 25 | CH₂ | 2 | H | H | NO₂ | H | Cl | 138 |
| 26 | CH₂ | 2 | H | H | NO₂ | H | F | 96 |
| 27 | CH₂ | 2 | H | H | NO₂ | H | OSO₂CH₃ | 167 |
| 28 | CH₂ | 2 | H | H | NO₂ | H | SO₂CH₃ | 160 |
| 29 | CH₂ | 2 | H | H | NO₂ | H | SCH₃ | 145–147 |
| 30 | CH₂ | 1 | H | H | NO₂ | H | SCH₃ | 126 |

The starting compounds of formula II herein are known or, in cases where they are not, can be produced by methods analogous to known methods or by methods described herein.

Thus, the enol esters of formula II can be prepared by the reaction of a 3,5-dione of formula III with a benzoyl halide of formula IV (wherein Q is a halogen atom) in the presence of a moderate base such as triethylamine.

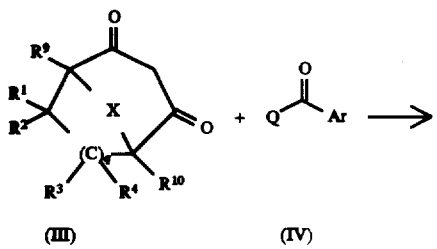

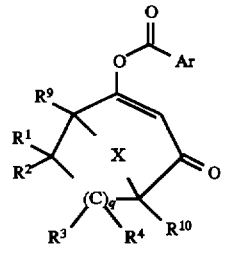

The bicycloalkane diones of formula III can be synthesized by the methods such as a) described by Hiroshi Kakisawa et al., *Bull. Chem. Soc. Jpn.*, 60:4369 (1987), or b) by oxidizing the known hydroxy-oxabicyclo[2,2,1]heptane (U.S. Pat. No. 4,670,041) to oxabicyclo[2,2,1]heptane-2,3-diones. Ring expansion of oxabicyclo[2,2,1]heptane-2,3-dione with alkyl diazoacetate (described by Korobitsyna et al., *J. Gen. Cheml USSR* 27:1859 (1957)) followed by heating in the presence of water, may also be used.

INTERMEDIATE COMPOUNDS

The following examples are presented to illustrate representative methods of preparing the intermediate compounds.

EXAMPLE 13

4-Chloro-2-nitrobenzoic acid (0.430 g, 2.13 mmol) is heated under reflux with thionyl chloride for 2 hr., after which excess thionyl chloride is removed under vacuum. The resulting acid chloride residue in 5 ml of methylene chloride is added to bicyclo[3,2,1]octane-2,4-dione (0.294 g, 2.13 mmol) dissolved in 10 ml of methylene chloride, with cooling to 0°, followed by dropwise addition of triethylamine (0.50 ml, 3.40 mmol). The mixture is stirred at RT for 30 min. and is then taken up in methylene chloride. The organic layer is washed with brine, dried and evaporated to give 4-(4-chloro-2-nitrobenzoyloxy)-bicyclo[3,2,1]-3-octen-2-one.

EXAMPLE 14

To a solution of (±) camphorquinone [(1,7,7)-trimethylbicyclo[3,2,1]-heptane-2,3-dione] (15.0 g, 90.24 mmol) and ethyl diazoacetate (11.8 g, 103.7 mmol) in 120 ml of ether is added, at 0°, $BF_3$.ether (4 ml). The mixture is stirred at RT for 24 hr. The reaction mixture is extracted with 5% $K_2CO_3/H_2O$ until no polar ethyl carboxyl dione remains. The combined aqueous extracts are acidified with conc. HCl and extracted with ether. The combined organic extracts are dried and evaporated to dryness to give crystalline 3-carboethoxy-1,8,8-trimethylbicyclo[3,2,1]octane-2,4-dione.

The above octane-2,4-dione (5.0 g, 19.8 mmol) in 20 ml of dimethylsulfoxide (DMSO) and 0.8 ml of water is heated at 130°–140° for 1 hr. The reaction mixture is diluted with ether, washed with water and with brine, dried and evaporated to give crystalline 1,8,8-trimethylbicyclo[3,2,1]-octane-2,4-dione, m.p. 220°.

EXAMPLE 15

To a solution of 1,8,8-trimethylbicyclo[3,2,1]octane-2,4-dione (2.0 g, 11.0 mmol) in 25 ml of methylene chloride containing triethylamine (2.30 ml, 16.0 mmol) is added, dropwise at 0°, a solution of 4-chloro-2-nitrobenzoyl chloride, prepared from the corresponding acid (2.23 g, 11.0 mmol) and thionyl chloride, in methylene chloride (5 ml). After the addition is complete, the mixture is warmed to RT and stirred for 1 hr. at RT, after which it is diluted with methylene chloride, washed, dried and evaporated to dryness to give a mixture of 4-(4-chloro-2-nitrobenzoyloxy)-5,8,8-trimethylbicyclo[3,2,1]-3-octen-2-one and 4-(4-chloro-2-nitrobenzoyloxy)-1,8,8-trimethylbicyclo[3,2,1]-3-octen-2-one.

EXAMPLE 16

To a solution of 4-hydroxy-3-methoxy-2-nitrobenzaldehyde (10.0 g, 50.7 mmol) in 200 ml of methylene chloride and containing triethylamine (10.60 ml, 1.5 eq.) at 0° is added methanesulfonyl chloride (4.32 ml, 6.39 g, 1.1 eq.) over a period of 5–10 min. The mixture is stirred for an additional 10 min., and is then washed with ice water, with dilute HCl, with sat. $NaHCO_3$ and with brine. The layers are separated and the organic layer is dried and evaporated to give 3-methoxy-4-methylsulfonyoxy-4-nitrobenzaldehyde.

The above aldehyde (13.25 g) is suspended in acetone and cooled to 0°. Jones reagent is added dropwise over approx. 15 min. until the solution is slightly orange, indicating an excess of the reagent. The reaction is stirred for approx. 1 hr., after which it is diluted with water and extracted with ethylacetate to give 3-methoxy-4-methylsulfonyloxy-2-nitrobenzoic acid.

EXAMPLE 17

3-Methoxy-4-methylsulfonyloxy-2-nitrobenzoic acid (5.13 g, 17.6 mmol) is heated under reflux with thionyl chloride for 2 hr., after which excess thionyl chloride is removed under vacuum. The resulting acid chloride residue is added to bicyclo[3,2,1]octane-2,4-dione (17.6 mmol) dissolved in 50 ml of methylene chloride, with cooling to 5°, followed by dropwise addition of triethylamine (3.19 ml, 1.3 eq.). The mixture is stirred at RT for 2 hr. and then poured into water. The organic layer is washed with brine, dried and evaporated to give 4-(3-methoxy-4-methylsulfonyloxy-2-nitrobenzoyloxy)bicyclo[3,2,1]-3-octen-2-one.

EXAMPLE 18

To a solution of 2-chloro-4-hydroxybenzoic acid (3.45 g, 20 mmol) and sodium hydroxide (2.40 g, 60.0 mmol) in 30 ml of water is added, dropwise at 0°, methanesulfonyl chloride (2.57 ml, 3.80 g, 33.0 mmol). After addition is complete, the reaction mixture is stirred at RT for 30 min., after which it is poured into water, acidified with dil. HCl and extracted with ether. The combined organic extracts are washed with brine, dried and evaporated to give 2-chloro-4-methylsulfonyloxybenzoic acid.

EXAMPLE 19

To a solution of bicyclo[3,2,1]octane-2,4-dione (14.0 mmol) in 20 ml of methylene chloride containing triethylamine (2.90 ml, 20.8 mmol) is added, dropwise at 0°, a solution of 2-chloro-4-methylsulfonyloxybenzoyl chloride, prepared from the corresponding acid (3.50 g, 14.0 mmol) and thionyl chloride, in methylene chloride (10 ml). After the addition is complete, the mixture is stirred for another 30 min. at 0°, after which it is diluted with methylene chloride, washed, dried and evaporated to dryness to give 4-(2-chloro-4-methylsulfonyloxybenzoyloxy)-bicyclo[3,2,1]-3-octen-2-one.

EXAMPLE 20

Silver oxide is prepared by adding a solution of silver nitrate (43.53 g, 0.26 mol) in 100 ml of water to a solution of sodium hydroxide (20.48 g, 0.51 mol) in 100 ml of water. To this brown semisolid mixture is added 6-nitropiperonal (25.0 g, 0.128 mol) in small portions with vigorous stirring. The reaction mixture is stirred for 2 hr. at 50°. The mixture is then filtered, and the filtrate is acidified, and extracted with ether. The ether extracts are dried and the ether evaporated off to give, after trituration with ether/hexane, 6-nitro-1,3-benzodioxole-5-carboxylic acid.

EXAMPLE 21

6-Nitro-1,3-benzodioxole-5-carboxylic acid (2.71 g) is heated under reflux with 25 ml of thionyl chloride for 2 hr., after which excess thionyl chloride is removed under vacuum. The resulting acid chloride residue is added to bicyclo[3,2,1]-octane-2,4-dione (11.8 mmol) dissolved in methylene chloride, with cooling to 5°, followed by dropwise addition of triethylamine (1.3 eq.). The mixture is stirred at RT for 2 hr. and then poured into water. The organic layer is washed with brine, dried and evaporated to give 4-(4,5-methylenedioxy-2-nitrobenzoyloxy) bicyclo-[3,2,1]-3-octen-2-one.

BIOASSAY

EXAMPLE F

Paddy soil in plastic pots (200 $cm^3$) was just flooded and then puddled. Water depth was maintained at 4 cm during testing without water drainage treatment. The field was seeded with barnyard-grass, monochoria, ammania and bulrush. The tubers of Sagittaria trifolia, pygmaea, water nutsedge and water chestnut were buried in the field. Six rice seedlings in a diphyllous stage (breed: Koshihikari, 1 cm plating: 3 rice seedlings, 3 cm plating: 3 rice seedlings) per pot were transplanted. After 10 days from the transplantation, the powder formulated according to Example E was spread over the surface of water. On the next day after the application and on the day after next, water was allowed to leak out at a rate of 3 cm/day. On the 21st day after the application, evaluation was made by observing degree of damage to the plants.

Excellent weed control is achieved with little or no rice crop damage at rates of 125 g/ha or less using e.g. compounds 8, 36 and 37.

EXAMPLE G a) Preemergent

Weeds and crop plants are seeded two per pot and covered with soil. The active ingredient is sprayed onto the surface of the soil at the chosen application rate with a spray volume equivalent to 600 L/Ha (50% acetone, ½% surfactant, remainder water). 4 pots per a.i. and species. Evaluation of percentage control takes place at 10 and 28 days post application.

b) Postemergent

Methodology as a) except that spraying takes place at the 2 leaf stage and evaluation of percentage control after 14 and 28 days.

Excellent control of both broadleaf and grassy weeds was obtained at 300 g/ha or less with low damage to corn and rice e.g. with compounds 8, 10 and 27.

What is claimed is:

1. A compound having the formula I

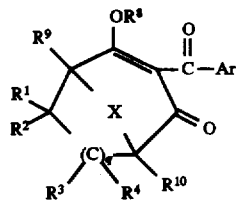

wherein,

Ar is selected from the groups

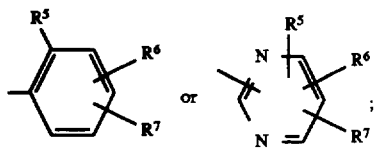

X is oxygen or;

each of $R^1$, $R^2$, $R^3$, $R^4$, $R^9$ and $R^{10}$ is, independently, hydrogen, $C_{1-8}$alkyl or $COOR^{16}$;

$R^5$ is $C_{1-8}$alkyl, optionally substituted with one to six halogen atoms; $C_{1-8}$alkoxy, optionally substituted with one to six halogen atoms; $C_{1-8}$alkylcarbonyl; $C_{1-8}$alkoxycarbonyl; $NR^{13}R^{14}$; $O_nS(O)_n \cdot R^{12}$; $NR^{15}SO_2R^{12}$; halogen; cyano; or nitro;

each of $R^6$ and $R^7$ is independently hydrogen or selected from the values of $R^5$; or $R^6$ and $R^7$ together form the group -Y-W-Z-;

$R^8$ is hydrogen, $C_{1-8}$alkyl, optionally substituted with one to four halogen atoms, $C_{1-8}$alkylcarbonyl, $C_{1-8}$alkoxycarbonyl, optionally substituted with one to four halogen atoms, $C(O)NR^{13}R^{14}$, $C_{1-8}$alkylsulfonyl, $P(O)-(OR^{11})_2$, $R^{13}P(O)OR^{11}$ or benzoyl or a salt forming moiety;

$R^{11}$ is $C_{1-8}$alkyl;

$R^{12}$ is $C_{1-8}$alkyl, optionally substituted with one to six halogen atoms;

each of $R^{13}$, $R^{14}$, $R^{15}$ and $R^{16}$ is, independently, hydrogen or $C_{1-8}$alkyl;

each of $R^{17}$ and $R^{18}$ is independently hydrogen, halogen, or $C_{1-8}$alkyl optionally substituted with one to six halogen atoms; or $R^{17}$ and $R^{18}$ together form an oxo group;

each of $R^{19}$ and $R^{20}$ is, independently, hydrogen, halogen, or $C_{1-8}$alkyl optionally substituted with one to six halogen atoms;

W is $-(CR^{17}R^{18})_t$, $-(CR^{19}R^{20})_t$— or $SO_2$;

each of Y and Z is independently oxygen, sulfur, $SO_2$, C=O or $CR^{15}R^{16}$; with the proviso that Y and Z are attached to adjacent carbons;

n is zero or one;

n' is zero, one or two;

q is zero, one or two;

t is one or two; and t' is zero or one.

2. A compound according to claim 1 wherein $R^8$ is hydrogen, $C_{1-8}$alkyl, $C_{1-8}$alkylcarbonyl, $C_{1-8}$alkoxycarbonyl, $C(O)NR^{13}R^{14}$, $C_{1-8}$alkylsulfonyl, $P(O)-(OR^{11})_2$, $R^{13}P(O)OR^{11}$ or benzoyl.

3. A compound according to claim 1 wherein $R^8$ is optionally substituted $C_{1-8}$alkylcarbonyl, optionally substituted $C_{1-8}$alkoxycarbonyl or optionally substituted benzoyl or is an ammonium salt derived from an amine of formula X

wherein each of $R^{21}$, $R^{22}$ and $R^{23}$ represents independently hydrogen, $C_{1-16}$alkyl optionally substituted by one or more hydroxy groups, $C_{2-4}$alkenyl or $R^{21}$ and $R^{22}$ form together a $C_{2-5}$alkylene group which may optionally be interrupted by oxygen.

4. A compound according to claim 1 wherein Ar is the group

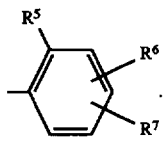

5. A compound according to claim 4 wherein X is oxygen q is one, and each of $R^1$, $R^2$, $R^3$, $R^4$, $R^9$ and $R^{10}$ is independently hydrogen or $C_{1-4}$alkyl.

6. A compound according to claim 5 wherein $R^5$ is $C_{1-4}$alkyl optionally substituted with one to three halogen atoms, $-(O)_n-S(O)_{n'}C_{1-4}$alkyl, halogen, or nitro.

7. A compound according to claim 6 wherein $R^5$ is methyl, $CF_3$, bromo, chloro, nitro or $OSO_2CH_3$ and $R^8$ is hydrogen, $C_{1-4}$alkyl, $C_{4-8}$alkylcarbonyl or benzoyl.

8. A compound according to claim 7 wherein $R^6$ is in the 3-position and is hydrogen, methoxy, chloro or $OSO_2CH_3$, and $R^7$ is in the 4-position and is methoxy, $CF_3$, bromo, chloro, nitro, $OSO_2R^{12}$ or $NHSO_2R^{12}$ where $R^{12}$ is methyl, $CH_2Cl$ or $CF_3$.

9. A compound according to claim 8 wherein $R^5$ is nitro and $R^6$ is hydrogen.

10. A compound according to claim 1 wherein X is oxygen and each of $R^1$, $R^2$, $R^3$, $R^4$, $R^9$, and $R^{10}$ is independently hydrogen, methyl or ethyl.

11. A compound according to claim 4 wherein, q is 1 or 2, $R^9$ and $R^{10}$ are hydrogen, $R^5$ is nitro or chloro, $R^6$ is hydrogen and $R^7$ is fluoro, chloro, bromo, S-$C_{1-4}$alkyl, $SO_2$-$C_{1-4}$alkyl, $OSO_2$-$C_{1-4}$alkyl.

12. A compound according to claim 11 wherein $R^8$ is hydrogen.

13. A compound according to claim 4 selected from those wherein $R^1$, $R^2$, $R^3$, $R^4$, $R^6$, $R^9$ and $R^{10}$ are hydrogen, $R^5$ is nitro and a) q is 1 and $R^7$ is p-$SCH_3$; or b) q is 1 and $R^7$ is p-$SO_2CH_3$; or c) q is 1 and $R^7$ is p-$OSO_2CH_3$; or d) q is 2 and $R^7$ os p-$OSO_2CH_3$.

14. A compound according to claim 13 wherein $R^8$ is hydrogen.

15. A compound according to claim 13 wherein $R^8$ is as defined in claim 4.

16. An agricultural composition comprising an effective amount of a compound according to claim 1 together with an agriculturally acceptable carrier.

17. A method for the control of weeds which comprises applying to the weed or its locus an herbicidally effective amount of a compound of formula I according to claim 1.

18. A method for selectively controlling weeds in rice which comprises applying to the weeds or their locus a herbicidally effective amount of a compound of formula I according to claim 1.

19. A compound according to claim 4 wherein X is O; $R^1$, $R^2$, $R^3$ and $R^4$ are hydrogen; $R^5$ is methyl, $CF_3$, $C_{1-3}$alkylsulfonyl, $C_{1-3}$alkylsulfonoxy, chloro, bromo or nitro; $R^6$ is hydrogen or together with $R^7$ methylenedioxy; $R^7$ is chloro, fluoro, bromo, $C_{1-4}$alkylthio, $C_{1-3}$alkylsulfonyl or $C_{1-3}$alkylsulfonyloxy, or together with $R^6$ methylenedioxy; $R^9$ and $R^{10}$ are independently hydrogen or $C_{1-3}$alkyl; and q is one or two.

20. A compound according to claim 19 wherein $R^8$ is other than hydrogen or a salt forming moiety.

21. An agricultural composition comprising an effective amount of a compound according to claim 2 together with an agriculturally acceptable carrier.

22. An agricultural composition comprising an effective mount of a compound according to claim 4 together with an agriculturally acceptable carrier.

23. A method for selectively controlling weeds which comprises applying to the weed or its locus an herbicidally effective amount of a compound according to claim 4.

* * * * *